United States Patent
Nessel et al.

(10) Patent No.: US 10,610,637 B2
(45) Date of Patent: Apr. 7, 2020

(54) METHOD OF PRIMING A MEDICAL PUMP

(71) Applicant: SANOFI-AVENTIS DEUTSCHLAND GMBH, Frankfurt am Main (DE)

(72) Inventors: Christian Nessel, Frankfurt am Main (DE); Robert Witt, Dresden (DE); René Richter, Dresden (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 303 days.

(21) Appl. No.: 15/547,448

(22) PCT Filed: Feb. 2, 2016

(86) PCT No.: PCT/EP2016/052171
§ 371 (c)(1),
(2) Date: Jul. 28, 2017

(87) PCT Pub. No.: WO2016/124589
PCT Pub. Date: Aug. 11, 2016

(65) Prior Publication Data
US 2018/0055994 A1     Mar. 1, 2018

(30) Foreign Application Priority Data
Feb. 2, 2015   (EP) .................................... 15153417

(51) Int. Cl.
*F04B 3/00*     (2006.01)
*A61M 5/142*    (2006.01)
(Continued)

(52) U.S. Cl.
CPC ............ *A61M 5/1422* (2013.01); *F04B 3/00* (2013.01); *F04B 13/00* (2013.01); *F04B 49/065* (2013.01);
(Continued)

(58) Field of Classification Search
CPC ...... F04B 13/00–02; F04B 3/00; F04B 7/045; F04B 19/22; F04B 49/005; F04B 49/12;
(Continued)

(56) References Cited

U.S. PATENT DOCUMENTS 2,673,519 A  *  3/1954  Halliburton  ............... F04B 3/00
                                                      74/44
2,705,835 A  *  4/1955  Massmann  ................ B65B 3/30
                                                      425/171
(Continued)

FOREIGN PATENT DOCUMENTS

FR            782769       6/1935
WO     WO2014/090745       6/2014

OTHER PUBLICATIONS

International Search Report and Written Opinion in International Application No. PCT/EP2016/052171, dated Apr. 11, 2016, 9 pages.
(Continued)

*Primary Examiner* — Charles G Freay
*Assistant Examiner* — Thomas Fink
(74) *Attorney, Agent, or Firm* — Fish & Richardson P.C.

(57) ABSTRACT

A method of priming a medical pump is disclosed. The method includes providing a medical pump comprising a chamber, a first plunger element and, a second plunger element. The method further comprises determining a minimum distance (MD) between the first and the second plunger element and determining the location of an opening of the chamber.

20 Claims, 12 Drawing Sheets

(51) Int. Cl.
*F04B 13/00* (2006.01)
*F04B 49/06* (2006.01)
*F04B 51/00* (2006.01)
*F04B 53/16* (2006.01)
*A61M 5/14* (2006.01)
*A61M 5/168* (2006.01)

(52) U.S. Cl.
CPC ............ *F04B 51/00* (2013.01); *F04B 53/162* (2013.01); *A61M 5/16809* (2013.01); *A61M 5/16827* (2013.01); *A61M 2005/1402* (2013.01)

(58) Field of Classification Search
CPC .. F04B 49/16; F04B 51/00; F04B 2201/0201; F04B 2201/0808; A61M 5/1422; A61M 5/16809; A61M 5/16827; A61M 2005/1402
See application file for complete search history.

(56) References Cited

U.S. PATENT DOCUMENTS

| | | | | |
|---|---|---|---|---|
| 3,471,079 | A * | 10/1969 | Myers | F01L 25/08 417/397 |
| 3,695,788 | A * | 10/1972 | Loomans | F04B 3/00 417/488 |
| 4,416,596 | A * | 11/1983 | Lichtenstein | F04B 7/045 222/137 |
| 5,639,220 | A * | 6/1997 | Hayakawa | F04B 7/045 347/30 |
| 6,004,117 | A * | 12/1999 | Brunk | F04B 13/00 417/488 |
| 2003/0003005 | A1 * | 1/2003 | Krieger | F04B 7/045 417/488 |
| 2004/0031488 | A1 * | 2/2004 | Terada | A61M 11/005 128/203.15 |
| 2004/0256422 | A1 * | 12/2004 | Penn | F16K 11/076 222/504 |
| 2007/0261677 | A1 * | 11/2007 | Bennion | F02B 25/08 123/51 R |
| 2008/0118376 | A1 * | 5/2008 | Verrilli | F04B 3/00 417/383 |
| 2011/0073620 | A1 * | 3/2011 | Verrilli | F04B 3/00 222/325 |
| 2014/0003968 | A1 * | 1/2014 | Gros-D'Aillon | C10J 3/30 417/53 |
| 2015/0025493 | A1 | 1/2015 | Eggert et al. | |
| 2015/0290389 | A1 * | 10/2015 | Nessel | F04B 3/00 604/500 |
| 2015/0297825 | A1 * | 10/2015 | Focht | A61M 5/142 604/151 |
| 2016/0213851 | A1 * | 7/2016 | Weibel | A61M 5/1422 |
| 2019/0201624 | A1 * | 7/2019 | Weibel | A61M 5/1422 |

OTHER PUBLICATIONS

International Preliminary Report on Patentability in International Application No. PCT/EP2016/052171, dated Aug. 8, 2017, 7 pages.

* cited by examiner

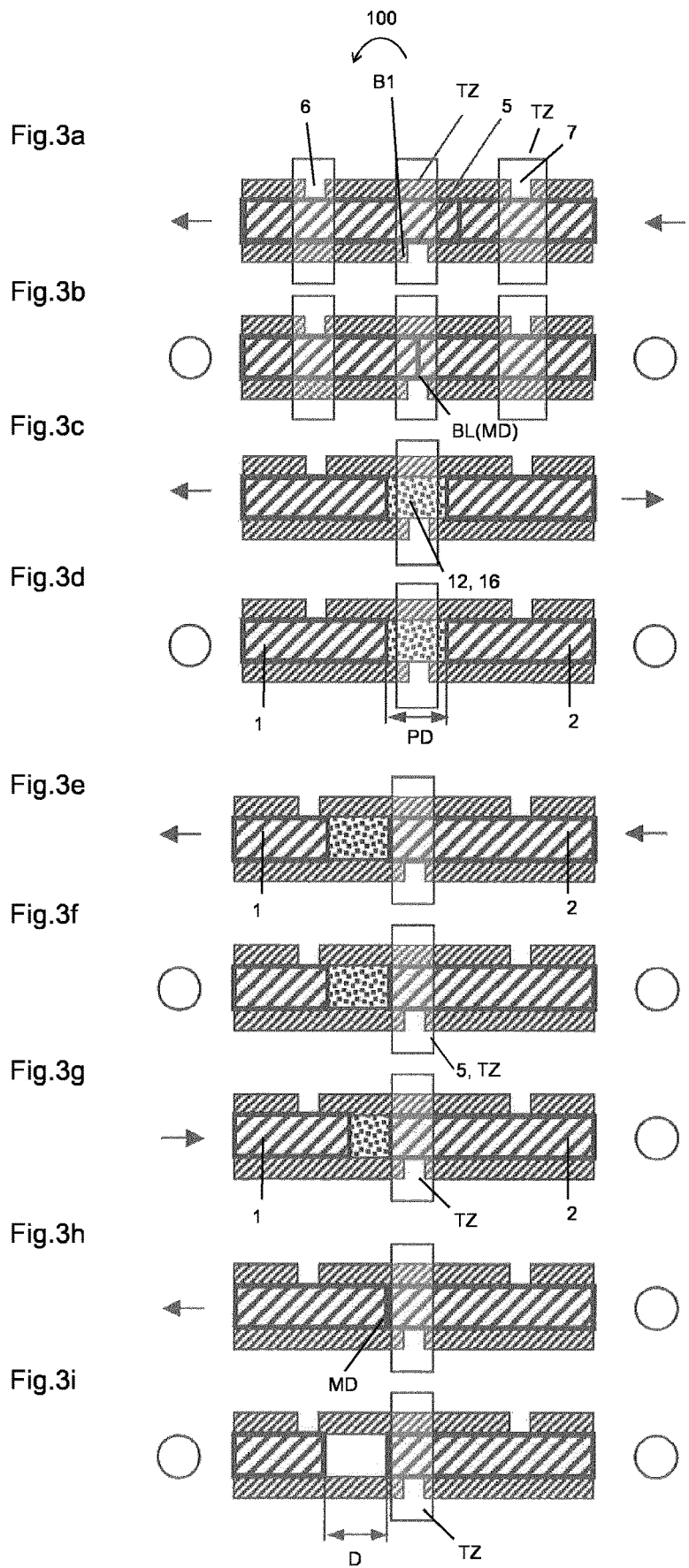

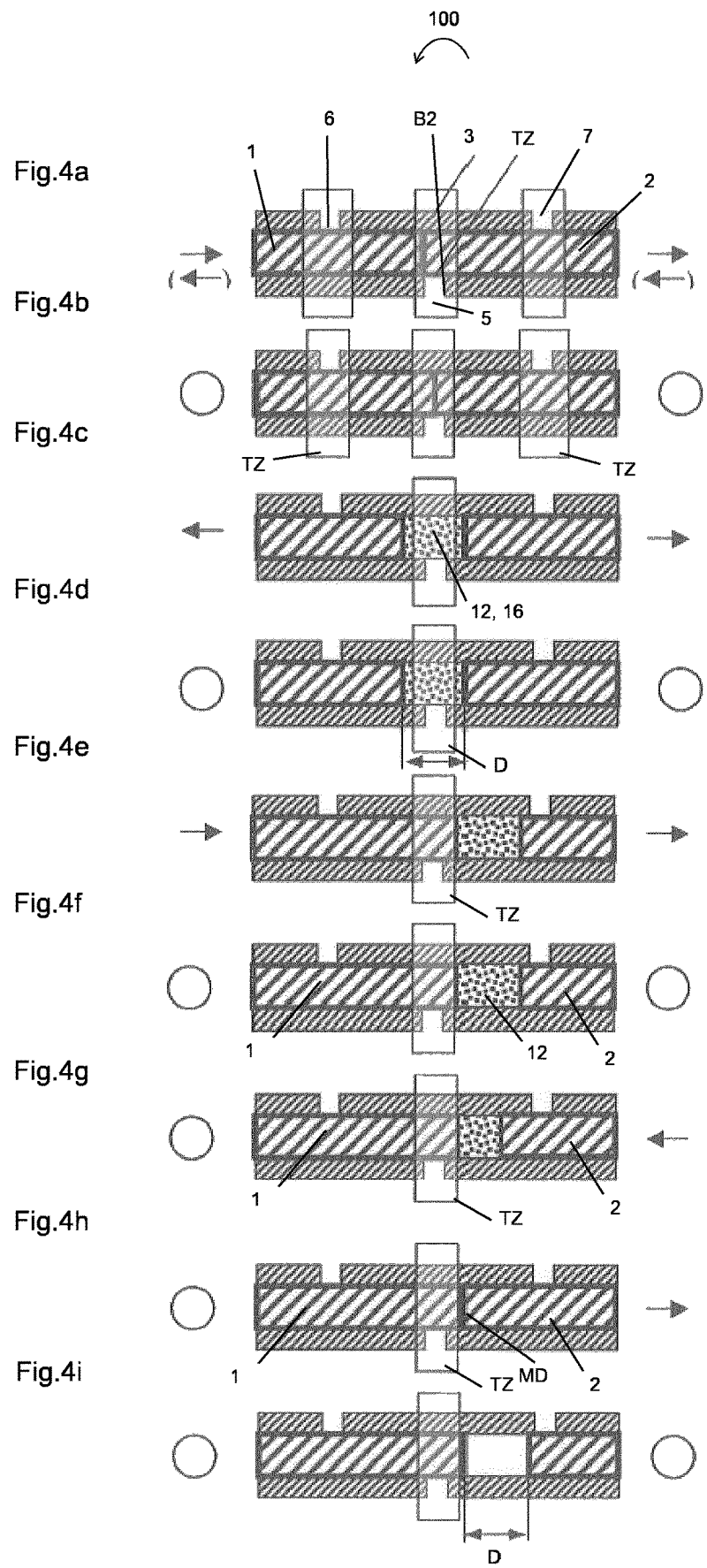

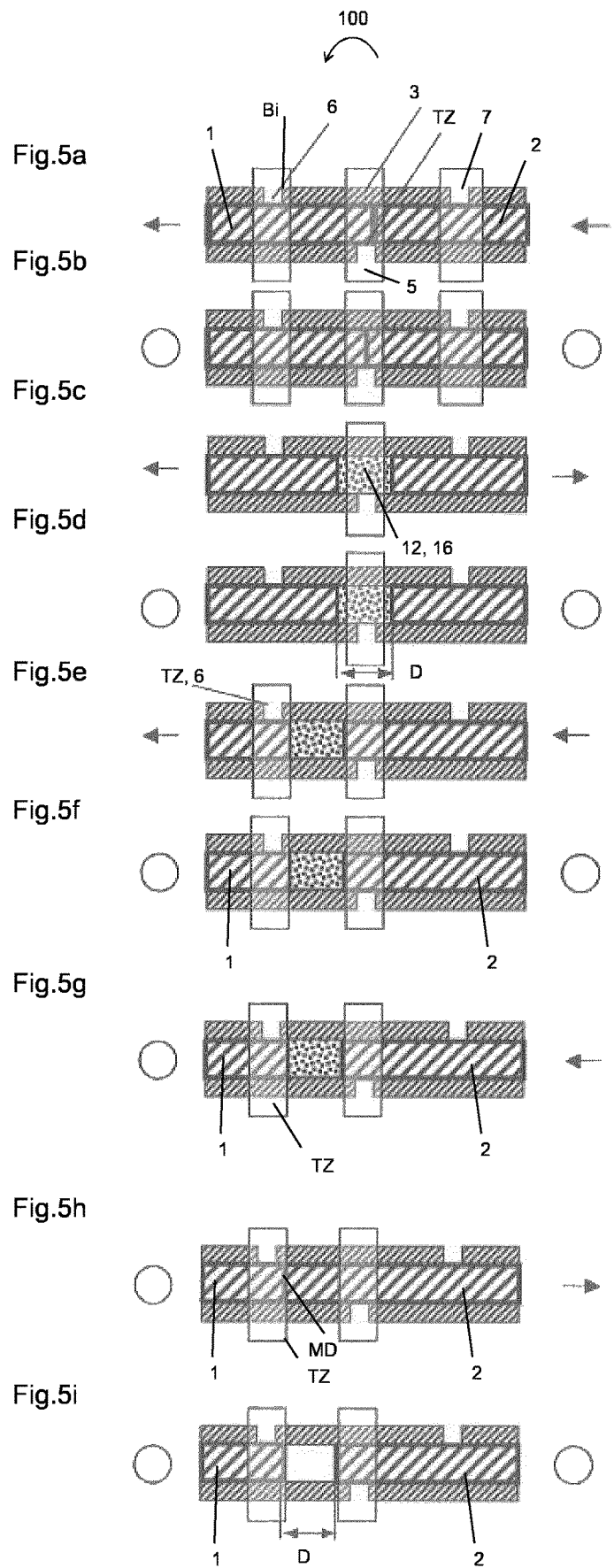

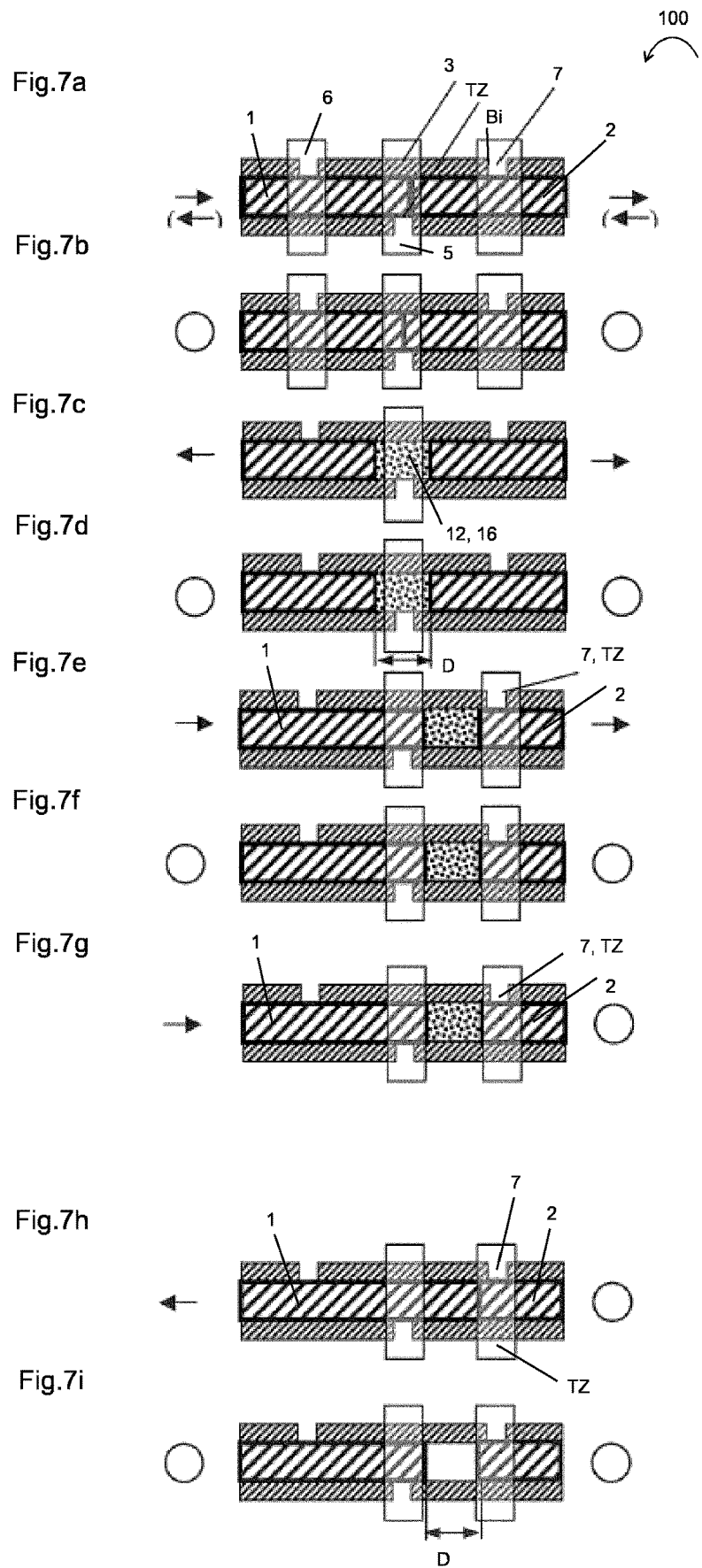

METHOD OF PRIMING A MEDICAL PUMP

CROSS REFERENCE TO RELATED APPLICATIONS

The present application is the national stage entry of International Patent Application No. PCT/EP2016/052171, filed on Feb. 2, 2016, and claims priority to Application No. EP 15153417.9, filed Feb. 2, 2015, the disclosures of which are expressly incorporated herein in their entirety by reference thereto.

TECHNICAL FIELD

The present disclosure relates to a method of priming a pump, particularly a boxer pump such as a medical pump for conveying a fluid or liquid.

BACKGROUND

A medical pump is described in WO 2014/090745 A1, for example.

SUMMARY

Certain aspects of the present disclosure provide an improved boxer pump, particularly a medical pump and/or for an improved operation of the pump.

In an example, a method of priming, preparing or calibrating a pump such as a medical pump is provided. The method comprises the steps of providing the medical pump. The medical pump comprises a chamber, a first plunger element and a second 20 plunger element. The first and the second plunger element are preferably arranged along a common longitudinal axis. The longitudinal axis preferably exhibits a longitudinal axis of the chamber. Expediently, the first and the second plunger element are arranged in the chamber. Further, the first and the second plunger element are preferably each axially movable in or with respect to the chamber independently from each other.

The mentioned priming, preparing or calibration of the pump preferably relates to or comprises the detection or localization of one or more openings of the chamber which may be necessary or expedient for an operation of the pump, e.g. conveying and/or delivering of a liquid or fluid.

The method further comprises determining or determination of a reference position of the first and the second plunger element. The determining of said reference position comprises determining of a minimum distance between the first and the second plunger element. The minimum distance expediently denotes the minimum of axial distances between the first and the second plunger element which are achievable in an operation of the medical pump. The minimum distance is preferably zero, wherein the first and the second plunger element expediently abut. Moreover, the reference position preferably comprises information about the absolute axial positions of each of the first and the second plunger element with respect to the chamber. Preferably, the reference position comprises removal positions of the first plunger element and the second plunger element at which e.g. a fluid may be or has just been removed from the chamber.

The method further comprises determining of the location of an opening of the chamber, particularly the determining of a boundary of the opening, for example by means of an iterative process, loop, approximation or an approximative iteration.

The determining or determination of the location comprises introducing of a fluid or test fluid into a chamber space. The fluid and/or the test fluid may comprise a drug or may be a drug-free fluid. The chamber space is defined by the first plunger element and the second plunger element, preferably or expediently such that the chamber space is arranged axially between the first and the second plunger element.

The method further comprises ejecting the fluid over or via the at least one opening, the location of which should be determined. The fluid is preferably ejected via the opening until the first and second plunger elements are arranged at the minimum distance relative to each other. In an embodiment, preferably after ejection of the fluid over the at least one opening, the location of the at least one opening can be determined, preferably based on the position of at least one of or both of the first and second plunger elements when the first and second plunger element are arranged at the minimum distance. The determined location may be recorded for future operation of the medical pump.

In an embodiment, the fluid fulfils a compression property requirement. This preferably means that said fluid is not completely compressible under compression by the first and the second plunger element of the medical pump. To this effect, the fluid, preferably, comprises or consists of a liquid, such as an air-free or gas-free liquid or a liquid with only a minor fraction of air or gas.

In an embodiment, before the location of the opening is determined, it is checked or detected, whether the fluid fulfils the, preferably preset or predetermined, compression property requirement. The check is expediently performed by compressing the fluid while the fluid is fluidly disconnected from an exterior of the chamber. For doing so, the chamber space may be displaced to a position where it is fluidly disconnected from the exterior by moving the plunger elements accordingly, preferably in unison. To compress the fluid the plunger elements may be moved relatively towards one another. When the fluid does not fulfil the compression property requirement, the fluid is removed from the chamber space and replaced with a new fluid, e.g. via the inlet described below, in the chamber space, preferably until the fluid in the chamber space does fulfil the compression property requirement.

In an embodiment, for a detection whether the fluid fulfils the compression property requirement, the fluid is compressed while being fluidly disconnected from an exterior of the chamber. If then, under compression of the fluid, i.e. by means of a relative movement of the first and the second plunger element towards each other until no further movement is possible, the distance between the first and the second plunger element equals the minimum distance, the method, preferably, comprises removing the fluid from the chamber. If, on the other hand, under compression of the fluid, the distance between the first and the second plunger element does not equal the minimum distance, the fluid, preferably, fulfils the compression property requirement as it cannot completely be compressed. As a consequence said fluid may be used for the method described herein.

In an embodiment, the chamber comprises an inlet for receiving the fluid or through which the fluid can be introduced into the chamber space.

In an embodiment, the chamber comprises an outlet for removing the fluid from the chamber. The inlet is axially spaced from the outlet or vice versa. The opening preferably represents the inlet and/or the outlet. For introducing the fluid, the inlet may e.g. be mounted to or fluidly connected with a fluid reservoir or substance reservoir and the fluid may be introduced into the chamber, expediently by an underpressure generated between the first and the second plunger element in that e.g. the first and/or the second plunger element is moved axially away from the respective other one of the first and the second plunger element.

Besides the inlet and the outlet, the chamber may comprise a further outlet (see below).

In an embodiment, determining the location of the at least one opening of the chamber comprises determining the location of at least one boundary, such as a rim or an edge, of the at least one opening. In an embodiment the determining of the location of the boundary comprises, expediently after the introducing of the fluid into the chamber space, moving the fluid which in turn expediently fulfils the compression property requirement—to a position axially spaced from a detection position of the opening. Particularly, the position is axially spaced from the mentioned detection position by a tolerance distance of the opening. In other words, the first and the second plunger element are preferably moved simultaneously to the mentioned position such that the fluid is also replaced in the same way.

In an embodiment the determining of the location of the boundary comprises compressing of the fluid at the position axially spaced from the detection position. Preferably, therefore, the one of the first and the second plunger element which is arranged facing towards the opening is axially locked. Then, during compression, the other one of the first and the second plunger element, is preferably moved towards the one which has been locked until no further movement is possible. If then, under compression of the fluid, the distance between the first and the second plunger element equals the minimum distance, the axial position of a borderline or border region between the first and the second plunger element is recorded as the location of the boundary of the opening. Preferably, the borderline is the interface between the first and the second plunger element.

If, on the other hand, under compression of the fluid, the distance between the first and the second plunger element does not equal the minimum distance, the method comprises moving the fluid to a position being arranged closer to the detection position, by a predetermined distance, and the fluid is compressed again as described above until the boundary of the mentioned opening is found. Then, the detection position is expediently reached during the approximation of the fluid towards the detection position. As the distance between the first and the second plunger element equals the minimum distance or amounts to zero, the fluid could escape through the opening as a consequence of the compression of the fluid or the movement of the first and the second plunger element towards each other. As the fluid could escape, the opening has been located. The current position of the first and/or second plunger element may be used to mark and/or record the position of the opening and/or its boundary.

The mentioned borderline between said plunger elements preferably indicates an abutment point of the first and the second plunger elements which is, when the boundary is localized, determined or detected axially arranged at the detection position. If, contrarily, under the compression of the fluid, the relative distance of the first and the second plunger element does not equal the determined or recorded minimum distance, the first and the plunger element are successively or iteratively moved to a position being arranged closer to the detection position by a (further) predetermined distance as described above.

In an embodiment, the medical pump comprises a driving unit being configured to drive or move the first and the second plunger element with respect to each other as well as with respect to the chamber.

The fluid is expediently compressed by means of relative movement of the first and the second plunger element until no further relative movement of the plunger elements towards each other is possible. In this context, said plunger elements may be controlled or driven by the driving unit which may comprise a step motor or similar means. By means of a failure detection or a fail step detection of said motors, it may for example be detected that said plunger elements can no further be moved towards each other, as said plunger elements may, e.g., abut each other.

In an embodiment, the predetermined distance is less than half of the diameter of the opening the location of which should be determined, preferably a quarter of the diameter of the opening or less than a quarter of the diameter of the opening. The predetermined distance is preferably greater than 1/10 of the diameter of the opening the location of which should be determined.

In an embodiment, the respective opening of the chamber, e.g. the outlet, has a diameter in a range of 0.25 mm to 1.5 mm.

In an embodiment, the predetermined distance ranges from 0.05 mm to 0.25 mm.

By means of the described method, the medical pump can advantageously be primed in that the boundaries of e.g. the inlet and/or the outlet of the chamber can be located in an automatic and/or iterative calibration routine which may be necessary for or eases the operation of the pump, e.g. when the pump chamber has to be changed and accurate positions of openings of the chamber are required for an accurate functioning and/or dosage of the fluid to be conveyed or delivered by the pump.

In an embodiment, the determining or determination of the minimum distance of the first and the second plunger element is carried out by an approximative iteration.

In an embodiment, the approximative iteration comprises moving of the first or the second plunger element to an arbitrary position in a tolerance zone of the opening.

In an embodiment the tolerance zone of the opening is defined by the nominal position, particularly the nominal axial position, of the opening and the driving tolerances of the driving unit.

In an embodiment, the tolerance distance is defined by a tolerance zone of or corresponding to the opening. The tolerance zone is preferably determined by operational tolerances of the first and the second plunger element with respect to the chamber of the pump. The tolerance zone may extend around or along an edge of the opening, e.g. up to a distance of ±0.75 mm from the edge.

In an embodiment, the determining of the minimum distance further comprises compressing and/or relatively moving the first and the second plunger element towards each other until no further relative movement is possible and recording the minimum (axial) distance of the first and the second plunger element from the iteration. Fluid may be or may not be present initially in the chamber space when the determining of the minimum distance is started. To determine the minimum distance, fluid in the chamber space is preferably ejected, such as via one opening of the chamber. Particularly, the minimum axial distance of the first and the second plunger elements can be recorded, e.g. by means of a recording unit or similar means in that, per iteration, the minimum value of the relative distance is recorded or registered and the overall minimum is defined as said minimum distance. During a second iteration of the determining process, the second plunger element is preferably moved to an arbitrary position which is expediently different from the one to which it has been moved in the first iteration.

As mentioned above, this iterative process as well as the iterative functioning of the overall priming method stand out for simple and reliable means for priming a medical pump, particularly to determine the location of one or more boundaries of the opening such as e.g. the inlet and the outlet.

In an embodiment, the tolerance zone of the outlet overlaps or extends over an axial extension of the opening.

In an embodiment, the method comprises, before the determining of the minimum distance, the first and the second plunger element to be moved axially away from each other until each of the first and the second plunger element abuts a stop. According to this embodiment, a reliable positional and/or reference information of both plunger elements is obtained or is obtainable which may be used to determine the location of the boundary of the opening, for example. The first and the second plunger element can in other words be retracted or extracted from the chamber such that e.g. the chamber space is maximized. This process step can particularly be expedient before e.g. a new chamber is introduced into the pump which may in turn be necessary if e.g. medical and/or body fluids are conveyed or administered by the medical pump in medical applications.

In an embodiment, the axial positions of the first and/or the second plunger element with respect to the chamber at which the minimum distance is determined are recorded as outlet or removal positions of the first and the second plunger element, respectively. By means of the removal positions, a reference may be given for the first and the second plunger element to which position said elements may e.g. be moved when fluid is to be removed or ejected from the chamber within the described method.

In an embodiment, the opening is the inlet and the boundary is a first, preferably axial, boundary of the inlet.

In an embodiment, the opening is the inlet and the boundary is a second, preferably axial, boundary of the inlet being arranged axially opposite to the first boundary.

In an embodiment, an axial extension of the inlet is defined by the first and the second boundary.

In an embodiment, the opening is the outlet and the boundary is an inner boundary of the outlet being arranged facing towards the inlet.

In an embodiment, the tolerance distance equals half of an axial extension of the opening.

In an embodiment, the opening is the outlet and the boundary is an outer boundary of the outlet being axially arranged such that the outer boundary faces away from the inlet.

In an embodiment, the tolerance distance equals the axial extension of the outlet.

In an embodiment, the chamber comprises a further opening as a second outlet and/or a second inlet, wherein the boundary is an inner and/or an outer boundary of the further opening.

In an embodiment, the medical pump comprises a recording unit being configured to record the minimum distance of the first and the second plunger element and the location of the boundary of the opening.

In an embodiment, the method comprising removing the fluid through the outlet, after the determining of the reference position.

The second aspect of the present disclosure relates to a medical pump comprising a control unit and being configured to carry out the method as described herein. The control unit may comprises the driving unit and the recording unit. Advantageously, by means of the control unit, the medical pump can be primed or operated autonomously and/or automatically without the necessity of procedural steps being carried out by a user of the medical pump. Particularly, the medical pump may carry out the steps of localizing or determining of the location of openings of the chamber autonomously and/or automatically by means of the control unit.

The term "fluid" or "liquid", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-I) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-Npalmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-Npalmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-w (ocarboxyheptadecanoyl)-des(B30) human insulin and B29-N-(o-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-lle-Giu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39), des Pro36 [Met(O)14, IsoAsp28] Exendin-4(1-39),
des Pro [Trp(O2)25, Asp28] Exendin-4(1-39),
des Pro [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro28 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(0)14 des Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(81-39)(Lys)6-NH2,
H-Asn-(Glu)5-Pro36, Pro37, Pro38 [Met(O)14, Trp(O2)25, Asp28] Exendin-4(1-39)-10 (Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ.

The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α, and δ have a constant region composed of three tandem Ig domains, and a hinge region for added flexibility; heavy chains μ and ε and have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The FC contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCI or HBr salts. Basic salts are e.g. salts having a cation selected from alkali or alkaline, e.g. Na+, or K+, or Ca2+, or an ammonium ion N+(RI)(R2)(R3)(R4), wherein RI to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Another aspect relates to a medical pump configured and/or operable to perform the method described above and below. The pump is expediently configured such that the method is performed before the pump is ready to be used and/or before the pump is used to eject a fluid drug into a body. Preferably, the medical pump is configured such that it can be operated only for drug delivery if the method to determine the location of one, more or all of the openings of the chamber of the pump has been carried out before.

Features which are described herein above and below in conjunction with different aspects or embodiments, may also apply for other aspects and embodiments.

BRIEF DESCRIPTION OF THE FIGURES

Further features and advantageous embodiments of the subject-matter of the disclosure will become apparent from the following description of the exemplary embodiment in conjunction with the figures, in which:

FIGS. 5a to 5k show schematically a process sequence of determining of a location of an inner boundary of an outlet of the medical pump.

FIGS. 7a to 7k show schematically a process sequence of determining of an inner boundary of a further opening of the medical pump.

Figure 1A:
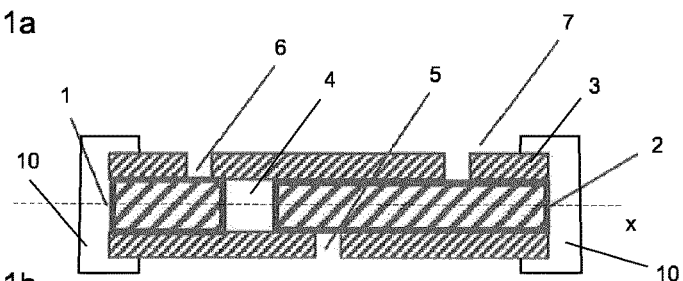
FIGS. 1a to 1c show schematically an initial process sequence of a priming method of a medical pump.

Like elements, elements of the same kind and identically acting elements may be provided with the same reference numerals in the figures. Additionally, the figures may be not true to scale. Rather, certain features may be depicted in an exaggerated fashion for better illustration of important principles.

DETAILED DESCRIPTION

The overall description by means of the figures is directed to a priming method of a pump 100, particularly a method of detecting or determining the location of an opening or a boundary thereof.

FIG. 1a shows a schematic of a pump 100 e.g. for conveying a liquid or fluid 12 (cf. FIG. 3c). The pump 100 comprises a first plunger element 1, a second plunger element 2 and a housing 3. Accordingly, the pump is expediently a boxer pump, as the first and the second plunger element 1, 2 are arranged oppositely.

The pump is preferably a medical pump 100 which may e.g. be operated as an infusion pump for delivering, particularly continuously delivering a subquantity of the liquid or fluid 12. Accordingly, the medical pump 12 may convey or deliver a medical substance, wherein the fluid 12 may be or comprise said medical substance.

Alternatively, the pump 100 may be any other kind of boxer pump, for example.

The housing 3 defines a chamber 4 in which the first and the second plunger element 1, 2 are oppositely arranged, thereby being movable along a common longitudinal axis x which preferably exhibits also the longitudinal axis of the chamber 4. The chamber 4 comprises—as an opening—an inlet 5, an outlet 6, e.g. a dispensing outlet, and a further outlet 7, e.g. a non-dispensing outlet or vent. Each of the outlet 6 and the further outlet 7 also exhibit openings of the chamber 4. The diameter of the respective opening may be 0.25 mm to 1.5 mm.

Alternatively, the further outlet may be a further inlet and the inlet may be the outlet.

Further, each of the first and the second plunger element 1, 2 are preferably axially movable in or with respect to the chamber 4, namely independently from each other.

Furthermore, the medical pump 100 may comprise a driving unit (not explicitly indicated in the figures) for driving and/or moving the first and the second plunger element. Said driving unit may e.g. comprise one or preferably at least two motors or step motors for driving the first and the second plunger element 1, 2, e.g. with respect to the housing 3 or the chamber 4.

The medical pump 100 further comprises a control unit 10 for controlling the driving unit and or the mentioned motors. The control unit 10 may comprise the driving unit and is indicated in FIG. 1 on both axial sides of the medical pump 100. Advantageously, by means of the control unit 10 carrying out the method steps described herein, the medical pump 100 can be primed or operated autonomously and/or automatically 20 without the necessity of procedural steps being carried out by a user of the medical pump.

Particularly, the medical pump 100 may carry out the steps of localizing or determining of the location of openings of the chamber autonomously and/or automatically by means of the control unit 10. Further, the control unit 10 may comprise a recording unit (not explicitly indicated) for recording e.g. an axial position of the first and the second plunger element 1 or a borderline of said plunger elements (see below). The recording unit may also record, the location a boundary of the opening 5, 6, 7 of the chamber 4 or e.g. of an axial distance between the first and the second plunger element 1, 2 (see below).

Moreover, the medical pump 100 is preferably configured such that the first and the second plunger element 1, 2 can selectively be locked with respect to the housing 3 or the chamber 4. The medical pump 100 may further comprises a substance reservoir (not explicitly indicated) containing liquid or fluid 12 e.g. with a medical substance or another fluid.

The outlet 6 and the further outlet 7 are arranged at a first side (upper side in FIG. 1) of the chamber 4 and the inlet 5 is arranged at a second side of the chamber 4 which is opposite from the first side. Moreover, the inlet 5 is arranged at an axial position between the outlet 6 and the further outlet 7.

The medical pump 100 is e.g. configured and operable to move the fluid e.g. from the substance reservoir into a chamber space 16 through the inlet 5. The chamber space 16 is preferably formed within the chamber 4 between the first plunger element 1 and the second plunger element 2.

Figure 1B:
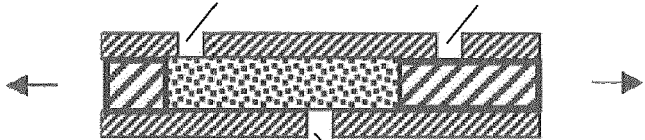
Figure 1C:
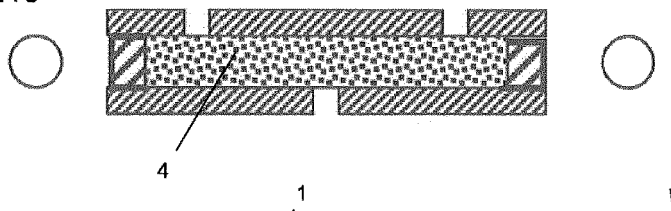

By means of FIGS. 1*a* to 1*c* an initial process sequence of the described method of the medical pump 100 is indicated. Particularly, as the absolute position of the first and the second plunger element 1, 2 with respect to the chamber may be unknown (cf. FIG. 1*a*), e.g. when a new chamber has been introduced or applied to the pump 100, a reliable positional or reference information of the first and the second plunger element 1, 2 may be desired.

In FIG. 1*b* it is shown that, then, the first and the second plunger element 1, 2 are or have been moved out of the chamber 4 or fully retracted to the position of the plunger elements 1, 2 shown in FIG. 1*c*. The circles on each axial side (i.e. left and right) of the medical pump 100 indicate that the plunger element which is arranged on the respective side is actually not moved but locked or has not been moved in the preceding step. On the other hand, the arrows on each side of the medical pump 100 indicate the direction in which the plunger element which is arranged on the respective side, is actually moved or has been moved in the preceding step (in FIG. 1*b* onwards, the control unit has not been indicated for simplicity reasons).

In the situation shown FIG. 1 *c*, the first and the second plunger element 1, 2 expediently each abut a mechanical stop (not explicitly indicated). This might be done preferably before inserting a new pump chamber. The relative positions of the first and the second plunger element 1, 2 with respect to the chamber 4 while abutting the stop may then be registered, detected or determined and/or stored by the control unit, e.g. for further positional calculations. Afterwards a reference position, e.g. comprising information of the relative axial distance of both plunger elements 1, 2 with respect to the chamber and/or about the minimum distance between the first and the second plunger element 1, 2 has to be determined.

In this regard, FIGS. 2*a* to 2*l* particularly indicate by means of the schematics, a process of determining of a minimum distance MD (cf. FIG. 2*l*) between the first and the second plunger element 1, 2 within the presented overall priming method. The minimum distance MD is preferably the minimum axial distance between the first and the second plunger element 1, 2 that can be reached during the operation of the medical pump 100. The minimum distance MD is preferably zero such that—in this case—the first and the second plunger element 1, 2 abut. The mentioned determining is carried out by an approximative iteration or iterative process comprising moving the first plunger element 1 or—without loss of generality—the second plunger element 2 to an arbitrary position in a tolerance zone TZ of the respective opening such as the further outlet 7. The tolerance zone TZ of the opening 5, 6, 7 is defined by the nominal position of the opening and the driving tolerances of the driving unit 10. Preferably, the tolerance zone is an axial area in which the respective opening 5, 6, 7 is arranged and in which the first and the second plunger element 1, 2 are arranged or arrangable under the consideration of the present inaccuracies and the nominal positions of the first and the second plunger element 1, 2 e.g., with respect to the chamber 4.

The determining of the minimum distance MD subsequently comprises relatively moving the first and the second plunger element 1, 2 towards each other until no further relative movement is possible. Additionally, possible air, gas or liquid which might initially have been present in the chamber 4 can be ejected therefrom in this way. This should preferably be carried out through the further outlet 7. So the touch spot, borderline or interface of both plunger elements should be at the further outlet 7 which may also be perceived as vent opening.

Figure 2A:
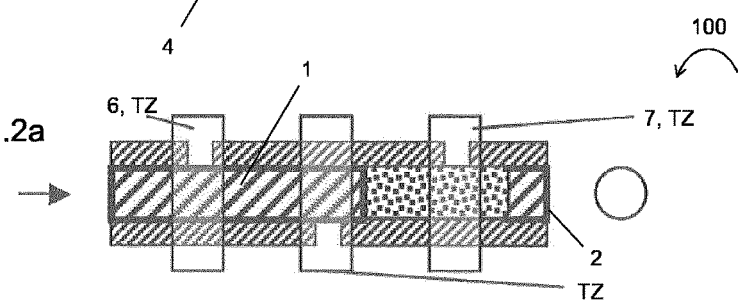
FIGS. 2a to 2l show schematically a partial process sequence of determining a reference position of a first and a second plunger element of the medical pump.

In FIG. 2*a*, particularly, the first plunger element 1 is moved or has been moved towards the second plunger element 2, which is locked.

Figure 2B:
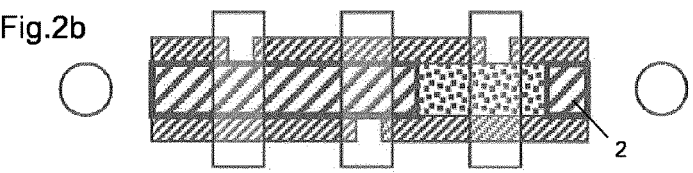
Figure 2C:
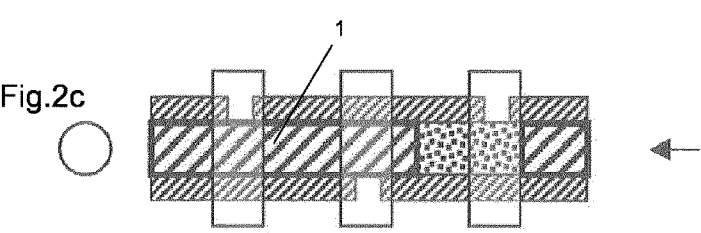
Figure 2D:
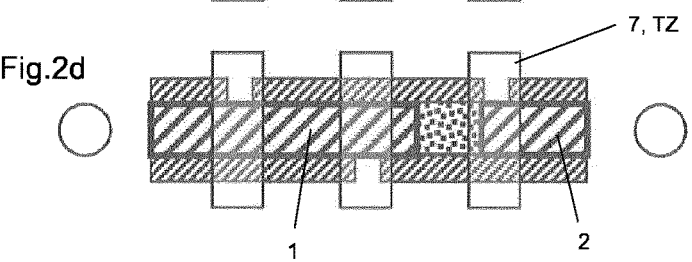

In FIG. 2*b*, also the first plunger element 1 is locked and subsequently, the second plunger element 2 is moved towards the first plunger element 1 (cf. FIG. 2*c*) and into the tolerance zone TZ of the further outlet 7 where the second plunger element 2 is locked (cf. FIG. 2*d*).

Figure 2E:
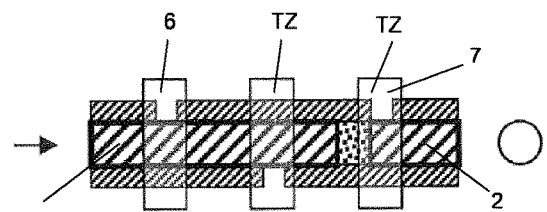
Figure 2F:
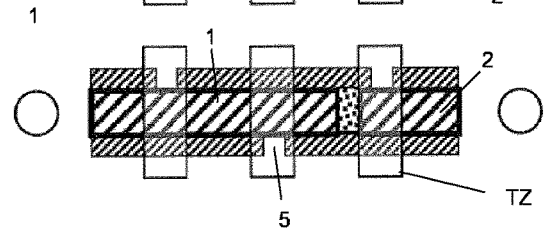

Consequently the first plunger element 1 is moved or driven in the direction or towards the second plunger element 2 until no further movement is possible as described above (cf. FIG. 2*e*). In FIG. 2*f*, the first plunger element 1 is locked as well. By means of a failure detection or a fail step detection e.g. of the motors of the driving unit, the driving unit and/or the control unit, it may be detected by any suitable means that said plunger elements 1, 2 can no further be moved towards each other, as the first and the second plunger element 1, 2 may, e.g., abut each other. This might be detected i.e. by significant increase of the driving current e.g. above a threshold current or force or by loss of steps when using a stepper motor as actuator or driver. The gap or minimum distance between both plunger elements 1, 2 may be defined by the sum of both plunger element extractions.

Said sum may be calculated or determined by the control unit and by means of the above mentioned positional information of both plunger elements 1, 2 when abutting the mentioned stops (cf. FIG. 1c).

Figure 2G:
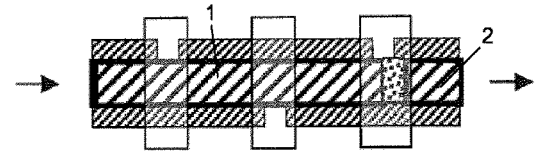
Figure 2H:
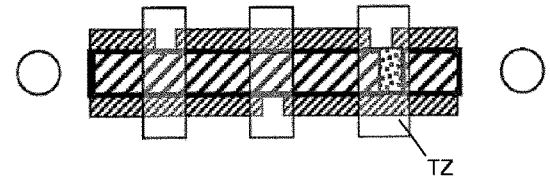
Figure 2I:
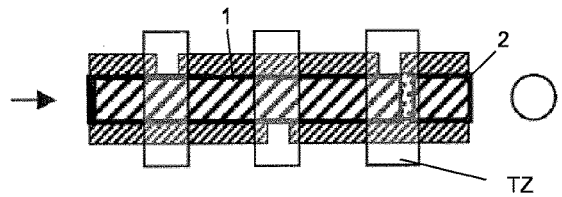
Figure 2J:
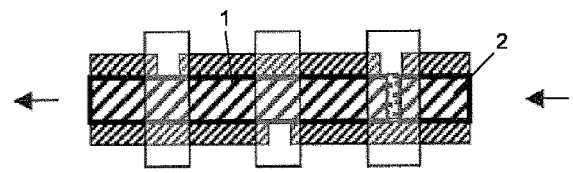
Figure 2K:
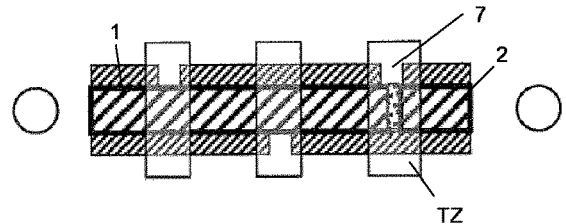
Figure 2L:
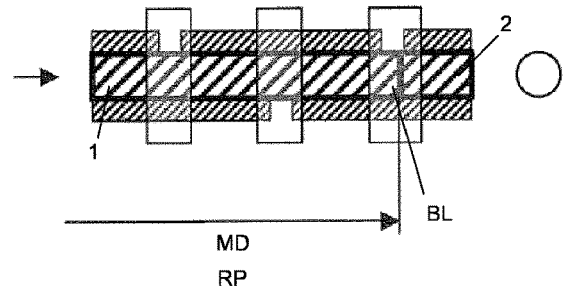

Now both plunger elements 1, 2 are—preferably simultaneously—moved to a different axial position (relative to the chamber 4) within the tolerance zone TZ of the further outlet 7, and the described procedure is repeated in a second iteration (cf. FIGS. 2g to 2i). This might be done several times, e.g. three times as described herein or even more times. Said third iteration is described in FIGS. 2j to 2l. The resulting minimum gap or minimum distance between the plunger elements 1, 2, derived from the sum of both plunger extractions (cf. above) is defined as plunger contact or a minimum distance MD of the plunger elements of zero. The more iterations are performed, the more accurate may be the result. In FIG. 2l, the minimum distance MD is determined after overall three iterations of the described process. Besides the minimum distance MD also the axial positions of the first and/or the second plunger element 1, 2 (with respect to the chamber 4) at which the minimum distance MD is determined are recorded as an outlet or removal position of the first and the second plunger element 1, 2. Consequently, the distance between both plungers is known as well as the absolute position of the touch point or borderline BL. Thereby a reference position RP is obtained which may be used for further calculations or evaluations during priming of calibration (cf. FIG. 2l).

Figure 3J:
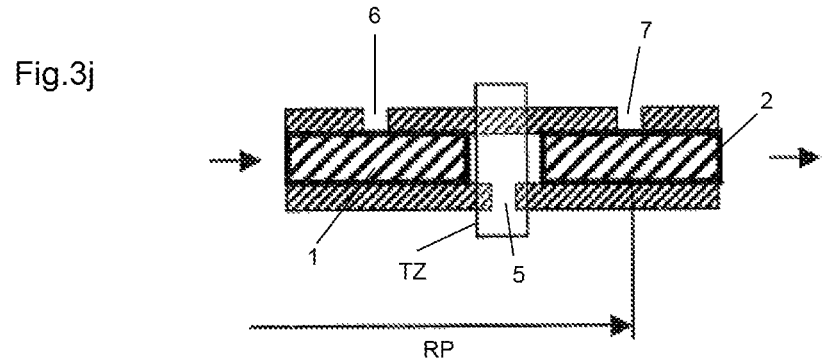
FIGS. 3a to 3n show schematically a process sequence of determining the location of a boundary of an inlet of a chamber of the medical pump.
Figure 3K:
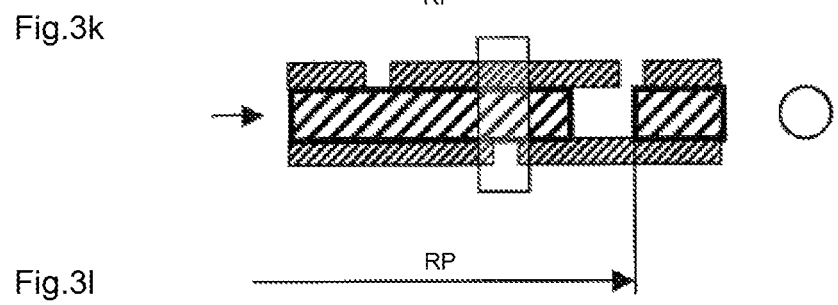
Figure 3L:
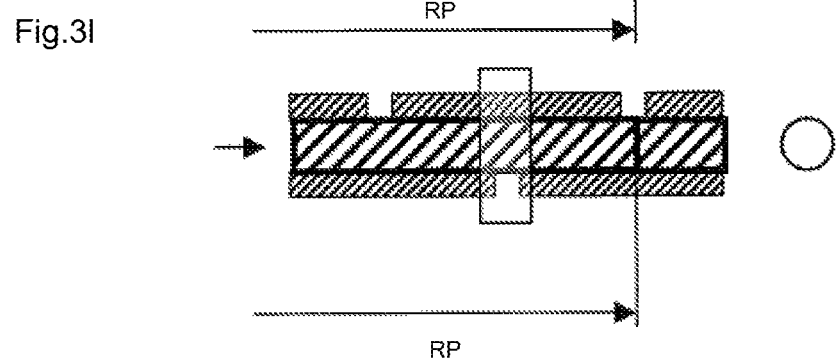
Figure 3M:
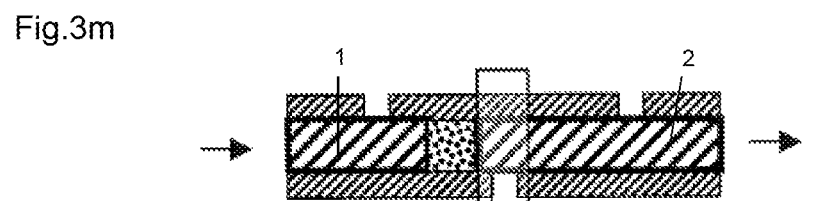
Figure 3N:
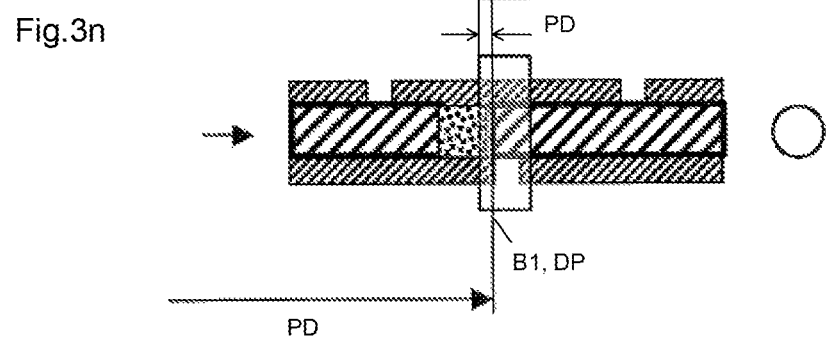

In FIGS. 3a to 3n, a boundary B1 (cf. FIG. 3n) of the inlet 5 or its location relative to the chamber 4 is determined. This process or sub-process of determining is an iterative process as well. Preferably, said process is an iterative approximation being carried out until the location of the boundary of the opening, in this case the inlet 5, is found.

Originating from the situation of FIG. 2l, both plunger elements 1, 2 are or have been moved simultaneously, i.e. preferably in contact with each other towards (cf. FIG. 3a) and into the tolerance zone TZ (cf. FIG. 3b) of the inlet 5 and are subsequently locked. The first and the second plunger element 1, 2 are then retracted or both moved away from each other such that a (test) volume of fluid or (test) fluid 12 is introduced into the chamber 4 by way of an underpressure generated between the first and the second plunger element 1, 2 by said relative movement (cf. FIG. 3c). Both plungers are then locked with respect to the chamber 4 again (cf. FIG. 3d).

For further evaluation or the further proceedings, it has to be verified, that the fluid 12 introduced into the chamber space 16 or a content of the chamber space 16 is suitable for the determining of the location of the boundary of the inlet 5 and, thus, fulfils a compression property requirement.

If the fluid 12 or the content of the chamber space 16 containing the fluid 12 fulfils or complies to the compression property requirement, it is preferably not completely compressible, as, then, (i.e. if it would be completely compressible) the chamber space 16 would preferably mainly comprise air or gas and the location of the respective boundary (cf. B1, B2 below) could not be determined. The compression property requirements mentioned herein are preferably predefined by any suitable measures. They may coincide or, alternatively differ from each other. By means of a detection whether the fluid 12 fulfils the compression property requirement, it is preferably assessed if gas or gas bubbles are present in the chamber space 16 along with the fluid 12 or liquid. Such gas may have entered the chamber 4 during the introduction of the fluid, due to leakage or gas bubbles present in the substance reservoir, for example. The relative movement of the first and the second plunger element 1, 2 tends to reduce or reduces the size of the chamber space 16.

For the detection if the fluid fulfils the compression property requirement, the fluid 12 and expediently the first and the second plunger element 1, 2 are moved to a position, at which the fluid 12 is fluidly disconnected from an exterior of the chamber 4, i.e. from an opening 5, 6, 7 of the chamber 4 (cf. FIG. 3e). Subsequently both plunger elements 1, 2 are locked (cf. FIG. 3f) and compressed by way of movement of e.g. the first plunger element 1 towards the second plunger element 2 until no further movement is possible (cf. FIG. 3g). If the resulting gap between the plunger elements 1, 2 is zero, the fluid 12 in the chamber space 16 is filled with air or gas which has to be removed from the chamber space 16. In FIG. 3h, it is shown that the mentioned fluid may be completely compressible as the plunger elements 1, 2 abut and/or the minimum distance MD is reached. This can particularly be detected, due to the previously performed determining of the minimum distance MD (see above).

Said removal is indicated in FIGS. 3i to 3l, wherein in FIG. 3k, the first plunger element 1 is moved back such that the first and the second plunger element 1, 2 are again spaced away from each other at a distance D as shown in FIG. 3f, for instance. Then, in FIG. 3i to 3l, it is shown that the fluid 12 is moved along with the plunger elements 1, 2 towards the further outlet 7 through which it is then removed from the chamber 4 as the second plunger element is locked at the recorded reference position RP or removal position of the second plunger element 2 (cf. FIG. 3l). By the method described up to now, the medical pump is preferably at the same time or automatically primed in terms of the movements of the plunger elements. Then, the presented method requires to introduce a further or new test volume as described in FIG. 3b onwards. Consequently, as gaseous fluid is removed before the method is continued, it is also ensured that any remaining gas between a reservoir with a liquid drug and the chamber 4 is removed before the method is continued. A gas or air-free pump conduit is facilitated in this way.

When, as suggested in FIG. 3g and/or 3h, under compression or movement of e.g. the first plunger element 1 towards the second plunger element 2 until no further movement is possible, the resulting gap or minimum distance between the plunger elements 1, 2 differs from zero, i.e. being greater than zero and/or the minimum distance MD the fluid 12 in the chamber space 16 fulfils the compression property requirement. In this case, the fluid 12 can be used to detect the location of the boundary B1 of the inlet 5. Therefore, the fluid 12 is moved or replaced by simultaneous movement of the plunger elements 1, 2 towards the tolerance zone TZ of the inlet 5 (cf. FIG. 3m). Particularly, the fluid 12 or as the case may be the inner side or end of the second plunger element 2 is moved near the tolerance zone TZ of the inlet 5, i.e. to a position axially spaced from a detection position DP of the inlet 5 at which the location of the boundary B1 can be determined or detected provided that the borderline BL of the first and the second plunger element 1, 2 is axially arranged at the detection position DP. The mentioned "spacing" of the position preferably relates to an axial spacing from the detection position DP by a tolerance distance T D. The tolerance distance TD is, in turn, preferably defined by the tolerance zone TZ of the inlet 5 or its extension. In other words, the tolerance distance TD is necessary in order not to miss the detection position DP during the approximation.

Then, as e.g. shown in FIG. 3n, the second plunger element 2 is locked and the first plunger element 1 compresses or moves the fluid 12 left i.e. towards the second plunger element 2. If, under this compression until no further movement is possible, the distance between the first and the second plunger element 1, 2 equals the minimum distance MD, the axial position of the borderline BL between the first and the second plunger element 1, 2 is recorded as the location of the boundary B1 of the inlet 5 as said boundary is found. If, on the other hand, under the compression, the distance D between the first and the second plunger element 1, 2 does not equal the minimum distance MD, the fluid 12 is moved (to the right in FIG. 3n) to a position being arranged closer to the detection position DP, by a predetermined distance PD. The predetermined distance PD is preferably the increment by which the approach towards or of the boundary B1 is carried out. The predetermined distance PD may range from 0.05 mm to 0.25 mm, for example.

This procedure is repeated until the minimum distance is finally reached or preferably until the resulting gap between both plunger elements 1, 2 is zero.

Figure 4J:
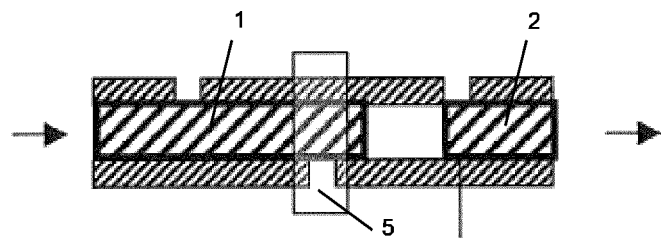
FIGS. 4a to 4n show schematically a process sequence of determining of a location of another boundary of the inlet.
Figure 4K:
Figure 4L:
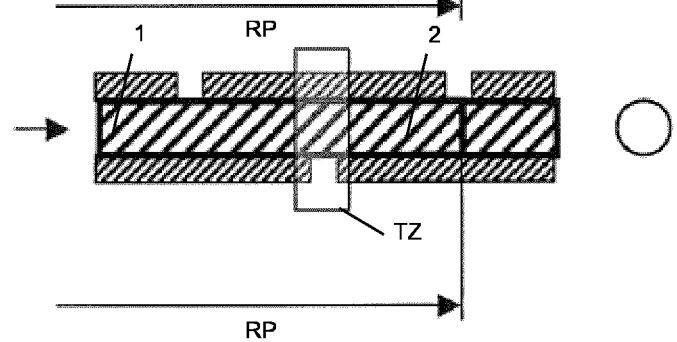
Figure 4M:
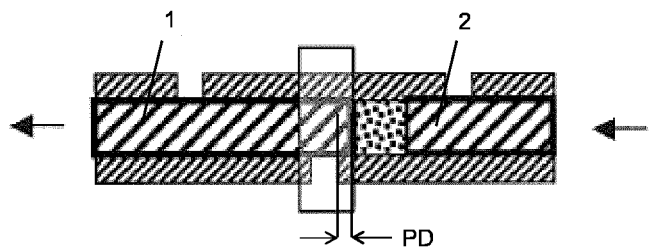
Figure 4N:

In FIGS. 4a to 4n, a second boundary B2 of the inlet 5 or its axial location is determined according or analogue to the determining of the location of boundary B1 (see above). The second boundary B2 is preferably arranged axially opposite to the abovementioned first boundary B1. The boundary B1 may be a first axial boundary of the inlet 5 and the second boundary B2 may be a second axial boundary of the inlet 5. Expediently, the first and the second boundary B1, B2 define an axial extension of the inlet 5.

At first, a new or further fluid 12 or test volume of fluid 12 has to be introduced into the chamber space 16. As described above, both plunger elements 1, 2 are moved simultaneously, and preferably in contact with each other, towards (cf. FIG. 4a) into the tolerance zone TZ (cf. FIG. 4b) of the inlet 5 and subsequently locked. The first and the second plunger element 1, 2 are then retracted or both moved away from each other such that the fluid 12 is introduced into the chamber 4 by way of a generated underpressure (cf. FIG. 4c). Both plungers are then again locked with respect to the chamber 4 (cf. FIG. 4d).

Now, it is again verified or checked, whether the fluid 12 introduced into the chamber space 16 fulfils the compression property requirement and is thus not completely compressible. Therefore, the fluid 12 and expediently the first and the second plunger element 1, 2 are moved to an position, at which the fluid 12 is fluidly disconnected from an exterior of the chamber 4 (cf. FIG. 4e). Subsequently both plunger elements 1, 2 are locked (cf. FIG. 4f) and compressed until no further relative movement of the first and the second plunger element 1, 2 is possible (cf. FIG. 4g). If the fluid 12 is completely compressible such that the plunger elements 1, 2 e.g. abut and/or the minimum distance MD is reached (cf. FIG. 4h), the fluid 12 has to be or is removed from the chamber space 16 (cf. FIGS. 4i to 4l and 3i to 3l and according description). Then, the presented method requires to introduce a further or new test volume as described in FIG. 4b onwards (cf. above).

When, as indicated in FIGS. 4g and e.g. 4h, the fluid 12 in the chamber space 16 fulfils 30 the compression property requirement, the fluid 12 can be used to detect the location of the second boundary B2 of the inlet 5. Therefore, the fluid 12 is again moved or replaced by simultaneous movement of the plunger elements 1, 2 towards the tolerance zone TZ of the inlet 5 (cf. FIG. 4m). Particularly, the fluid 12 or as the case may be the inner side or end of the first plunger element 1 is moved near or slightly towards the tolerance zone TZ of the inlet 5, i.e. to a position axially spaced from a detection position DP of the inlet 5 at which the location of the second boundary B2 can be determined or detected. Said position is preferably axially spaced from the detection position by a tolerance distance TD being in turn defined by the tolerance zone TZ of the inlet 5 or its extension. Then, as e.g. shown in FIG. 4n, the first plunger element 1 is locked and the second plunger element 2 compresses or moves the fluid 12 right, i.e. towards the first plunger element 1. If, under this compression or movement until no further movement is possible, the distance D between the first and the second plunger element 1, 2 equals the minimum distance MD, the axial position of the borderline BL 10 between the first and the second plunger element 1, 2 is found and recorded or registered as the location of the second boundary B2 of the inlet 5. If, on the other hand, under said compression, the distance D between the first and the second plunger element 1, 2 does not equal the minimum distance MD, the fluid 12 is moved to a position being arranged closer to the detection position DP by a predetermined distance 15 PD which preferably equals the above-mentioned predetermined distance in the context of the determining of the location of the first boundary B1. Alternatively, the predetermined distances mentioned herein may differ from each other. This procedure is repeated until the minimum distance is finally reached or preferably the resulting gap between both plunger elements 1, 2 is zero.

In FIGS. 5a to 5k, an inner boundary Bi of the outlet 6 or its axial location is assessed essentially according or analogue to the determining of the location of the first boundary B1 for example. The inlet 5 is preferably arranged axially between the outlet 6 and the further outlet 7.

Figure 5J:
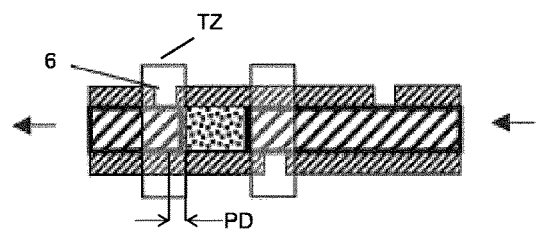

The inner boundary Bi is preferably arranged facing axially towards the inlet 5 (cf. FIG. 5a). As e.g. described in FIG. 3a to 3d or 4a to 4d, at first, a respective fluid 12 has to be introduced into the chamber space 16 (cf. FIGS. 5a to 5d). Now, it is again verified or checked, whether the fluid 12 introduced into the chamber space 16 fulfils the compression property requirement, and is thus not completely compressible. Therefore, the first and the second plunger element 1 and with it the fluid 12 are moved to a position, at which the fluid 12 is fluidly disconnected from an exterior of the chamber 4 (cf. FIG. 5e). Subsequently both plunger elements 1, 2 are locked (cf. FIG. 5f) and compressed until no further relative movement of the first and the second plunger element 1, 2 is possible (cf. FIG. 5g). If the fluid 12 is completely compressible such that the plunger elements 1, 2 e.g. abut and/or the minimum distance MD is reached (cf. FIG. 5h), the presented method requires again to remove the fluid 12 from the chamber space 16 (cf. FIGS. 4i to 4l for instance). Then, a new fluid 12 is introduced into the chamber 4 as described in FIG. 5b onwards (cf. above). When, as indicated in FIGS. 5g and e.g. 5h, the fluid 12 in the chamber space 16 fulfils the compression property requirement, the fluid 12 can be used to detect the location of the inner boundary Bi of the outlet 6. In FIG. 5i, the fluid 12 has been decompressed to its original volume again. Therefore, the fluid 12 is again moved or replaced towards the tolerance zone TZ of the outlet 6 (cf. FIG. 5j). Particularly, the fluid 12 or as the case may be the inner side or end of the first plunger element 1 is moved near and/or towards the tolerance zone TZ of the outlet 6, i.e. to a position axially spaced from the respective detection position DP of the outlet 6 at which the location of the inner boundary Bi can be determined or detected. Said position is preferably axially spaced from the detection position DP by the respective tolerance distance TD.

Preferably, the tolerance distances TD of the openings 5, 6, 7 described herein, coincide. Alternatively, the various tolerance distances TD may differ.

Figure 5K:
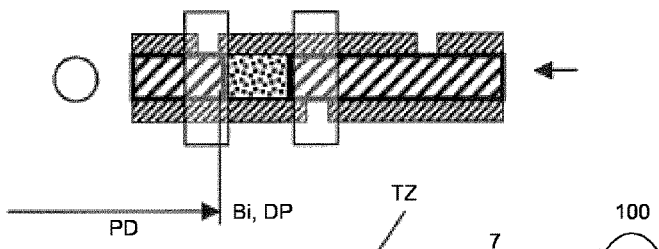

Then, as e.g. shown in FIG. 5*k*, the first plunger element 1 is locked and the second plunger element 2 compresses or moves the fluid 12 right, i.e. towards the first plunger element 1. If, under this compression, the distance D between the first and the second plunger element 1, 2 equals the minimum distance MD, the axial position of the borderline BL between the first and the second plunger element 1, 2 is found and recorded as the location of the inner boundary Bi of the outlet 6 by the recording unit. If, on the other hand, under said compression, the distance D between the first and the second plunger element 1, 2 does not equal the minimum distance MD, the fluid 12 is moved (to the left in FIG. 5*j*) to a position being arranged closer to the detection position DP, by the respective predetermined distance PD. This procedure is repeated until the minimum distance MD is finally reached or preferably the resulting gap between both plunger elements 1, 2 is zero.

According to the described embodiments, the tolerance distance expediently equals half of the axial extension of the respective opening, i.e. the inlet 5 or the outlet 6, respectively. The tolerance distance may also be lower. The tolerance distance may be ±0.75 mm.

In FIGS. 6*a* to 6*m*, an outer boundary Bo of the outlet 6 or its location relative to the chamber 4 is determined essentially according or analogue to the determining of the location of the first boundary B1 of the inlet 5, for example.

Figure 6A:
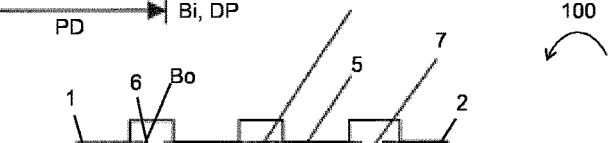
FIGS. 6a to 6m show schematically a process sequence of determining of an outer boundary to the outlet of the medical pump.
Figure 6B:
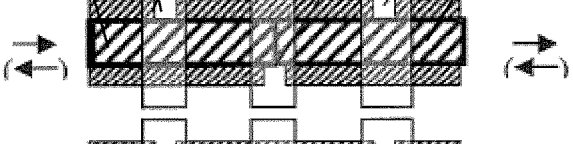
Figure 6C:
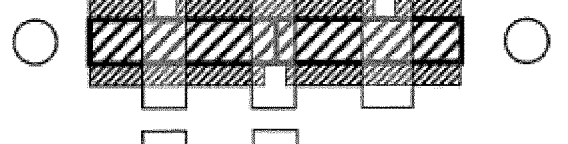
Figure 6D:
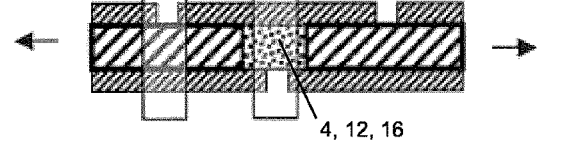

The outer boundary Bo is preferably arranged facing axially away from the inlet 5 (cf. FIG. 6*a*). As e.g. described in FIG. 3*a* to 3*d* or 4*a* to 4*d*, at first, a respective fluid 12 has to be introduced into the chamber space 16 (cf. FIGS. 6*a* to 6*d*). Now, it is again verified or checked, whether the fluid 12 introduced into the chamber space 16 fulfils the compression property requirement, and is thus not completely compressible.

Figure 6E:
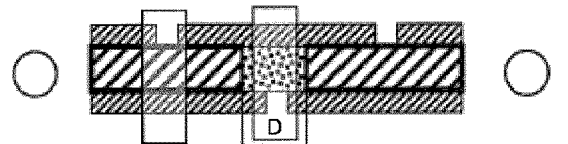
Figure 6F:
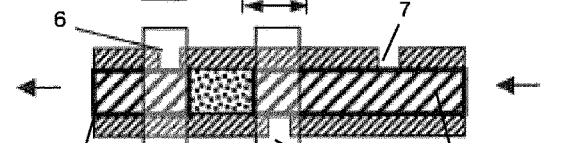
Figure 6G:
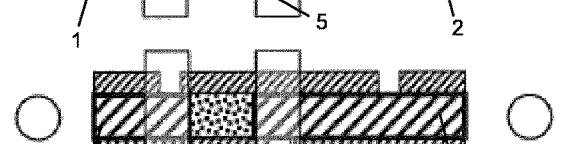
Figure 6H:
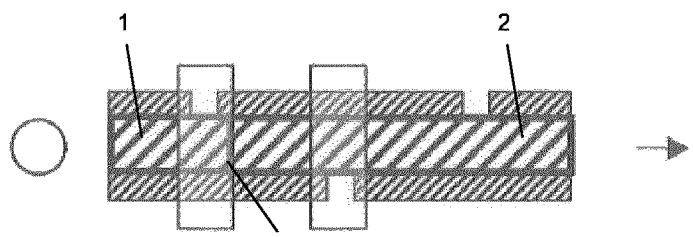
Figure 6I:
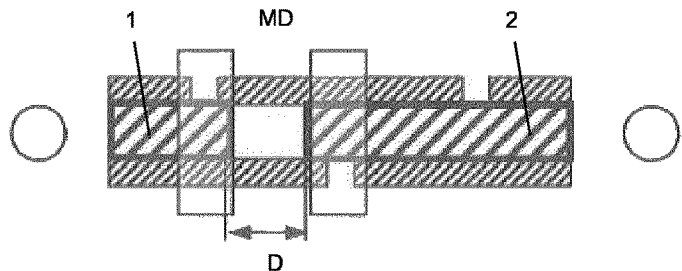
Figure 6J:
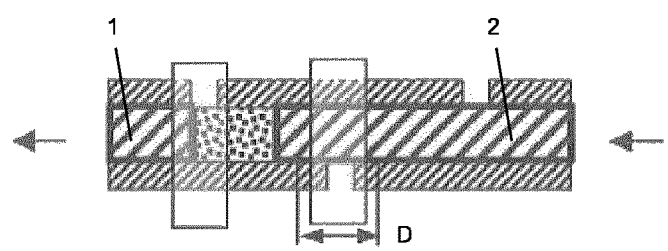
Figure 6K:
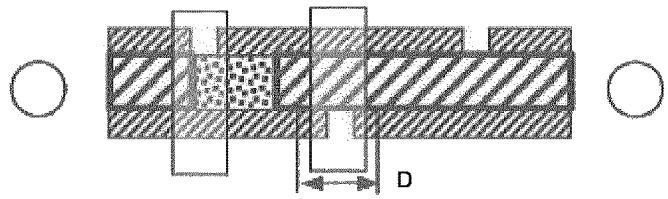

Therefore, the first and the second plunger element 1, 2 and with it the fluid 12 are moved to a position, at which the fluid 12 is fluidly disconnected from an exterior of the chamber 4 (cf. FIG. 6*e*). Subsequently both plunger elements 1, 2 are locked (cf. FIG. 6*f*) and compressed until no further relative movement of the first and the second plunger element 1, 2 is possible (cf. FIG. 6*g*). If the fluid 12 is completely compressible such that the plunger elements 1, 2 e.g. abut and/or the minimum distance MD is reached (cf. FIG. 6*h*), the presented method requires again to remove the fluid 12 from the chamber space 16 (cf. FIGS. 4*i* to 4*l* for instance). Then, a new fluid 12 is introduced into the chamber 4 as described in FIG. 6*b* onwards. When, as e.g. indicated in FIG. 6*g*, the fluid 12 in the chamber space 16 fulfils the respective compression property requirement, the fluid 12 can be used to detect the location of the outer boundary Bo of the outlet 6. Therefore, the fluid 12 is, then, after a decompression by (back-)movement of the second plunger element 2 (cf. FIG. 6*i*) replaced towards the tolerance zone TZ of the outlet 6 (cf. FIG. 6*j*). Particularly, the fluid 12 or as the case may be the inner side or end of the first plunger element 1 is moved towards the tolerance zone TZ of the outlet 6.

Said position is preferably axially spaced from the detection position DP by the respective tolerance distance TD.

Figure 6L:
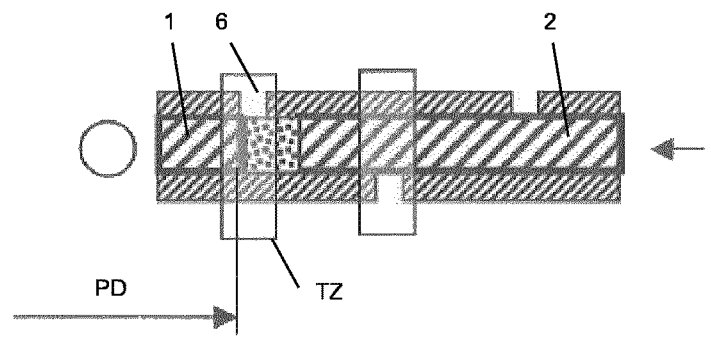
Figure 6M:
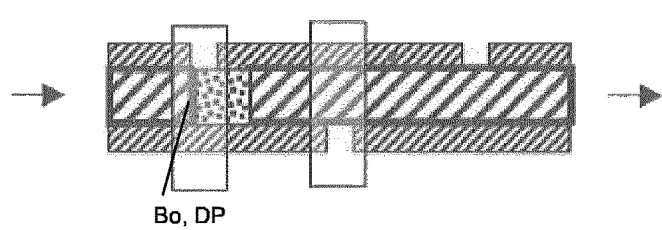

Then, as e.g. shown in FIG. 6*l*, the first plunger element 1 is locked and the second plunger element 2 compresses or moves the fluid 12 towards the first plunger element 1 from the right to the left. If, under this compression, the distance D between the first and the second plunger element 1, 2 equals the minimum distance MD, the axial position of the borderline BL between the first and the second plunger element 1, 2 is found and recorded as the location of the outer boundary Bo of the outlet 6 by the recording unit. If, on the other hand, under said compression, the distance D between the first and the second plunger element 1, 2 does not equal the minimum distance MD, the fluid 12 is moved (to the right in FIG. 6*m*) to a position being arranged closer to the detection position DP, by the respective predetermined distance PD. A movement as shown in FIG. 6*m* may (also) be suitable if there is a step between the boundary of the outlet and the first plunger element 1, for example in a situation similar to FIG. 6*l*, if the first plunger element is arranged more to the left. This would lead to fluid being trapped between the two plunger elements 1, 2. Then the plunger elements 1, 2 are displaced to 15 the right and the trapped fluid can also be dispensed via the opening (outlet 6). The procedure described above is repeated until the minimum distance MD is finally reached and/or preferably the resulting gap between both plunger elements 1, 2 is zero.

According to the described embodiments, the tolerance distance expediently equals or amounts to the axial extension of the respective opening, i.e. the outlet 6.

In FIGS. 7*a* to 7*k*, an inner boundary Bi of the further outlet 7 or its axial location is determined according or analogue to the determining of the location of the inner boundary Bi of the outlet 6 (cf. FIGS. 5*a* to 5*k*).

Figure 7J:
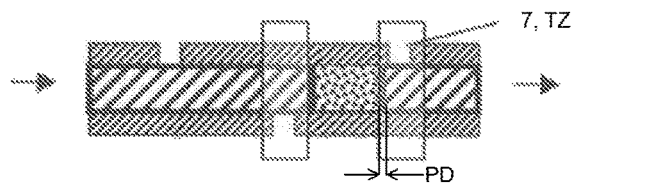

The inner boundary Bi of the further outlet 7 is preferably arranged facing axially towards the inlet 5 (cf. FIG. 7*a*). As e.g. described in FIGS. 3*a* to 3*d* or 4*a* to 4*d*, at first, a respective fluid 12 has to be introduced into the chamber space 16 (cf. FIGS. 7*a* to 7*d*). Now, it is again verified or checked, whether the fluid 12 introduced into the chamber space 16 fulfils the compression property requirement and is, thus, not completely compressible. Therefore, the first and the second plunger element 1, 2 and with it the fluid 12 are moved to a position, at which the fluid 12 is fluidly disconnected from an exterior of the chamber 4 (cf. FIG. 7*e*). Subsequently both plunger elements 1, 2 are locked (cf. FIG. 7*f*) and compressed until no further relative movement of the first and the second plunger element 1, 2 is possible (cf. FIG. 7*g*). If the fluid 12 is completely compressible such that the plunger elements 1, 2 e.g. abut and/or the minimum distance MD is reached (cf. FIG. 7*h*), the presented method requires again to remove the fluid 12 from the chamber space 16 (cf. FIGS. 4*i* to 4*l* for instance). Then, a new fluid 5 12 is introduced into the chamber 4 as described in FIG. 7*b* onwards. When, as e.g. indicated in FIG. 7*g*, the fluid 12 in the chamber space 16 fulfils the respective compression property requirement, the fluid 12 can be used to detect the location of the inner boundary Bi of the further outlet 7. In FIG. 7*i*, the fluid 12 has been decompressed to its original volume again. Therefore, the fluid 12 is again moved or replaced towards the tolerance zone TZ of the outlet 6 (cf. FIG. 7*j*). Particularly, the fluid 12 or as the case may be the inner side or end of the second plunger element 2 is moved near or close towards the tolerance zone TZ of the further outlet 7, i.e. a position axially spaced from the respective detection position DP of the further outlet 7 at which the location of the inner boundary Bi of the further outlet 7 can be determined or detected. Said position is preferably axially spaced from the detection position DP by the respective tolerance distance TD.

Figure 7K:
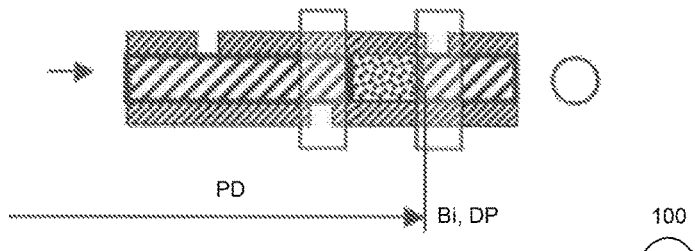

Then, as e.g. shown in FIG. 7k, the second plunger element 2 is locked and the first plunger element 1 compresses or moves the fluid 12 right, i.e. towards the second plunger element 2. If, under this compression, the distance D between the first and the second plunger element 1, 2 equals the minimum distance MD, the axial position of the borderline BL between the first and the second plunger element 1, 2 is found and recorded as the location of the inner boundary Bi of the further outlet 7 by the recording unit. If, on the other hand, under said compression, the distance D between the first and 25 the second plunger element 1, 2 does not equal the minimum distance MD, the fluid 12 is moved (to the right in FIG. 7j) to a position being arranged closer to the detection position DP, by the respective predetermined distance PD. This procedure is repeated until the minimum distance MD is finally reached or preferably the resulting gap between both plunger elements 1, 2 is zero.

In FIGS. 8a to 8m, an outer boundary Bo of the further outlet 7 or its location relative to the chamber 4 is determined essentially according or analogue to the determining of the location of the outer boundary Bo of the further outlet 7 (cf. FIGS. 6a to 6m).

Figure 8A:
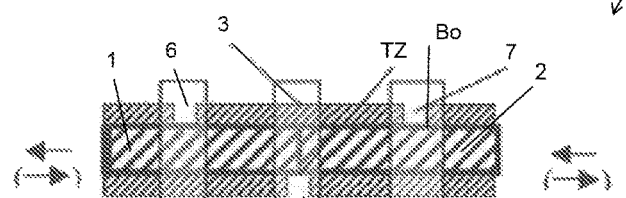
FIGS. 8a to 8m show schematically a process sequence of determining an outer boundary of the further opening of the medical pump.
Figure 8B:
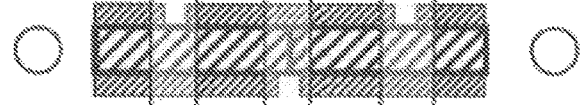
Figure 8C:
Figure 8D:
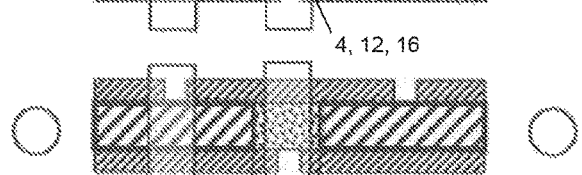
Figure 8E:
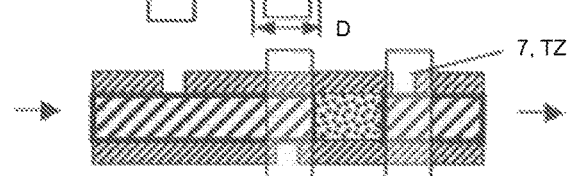
Figure 8F:
Figure 8G:
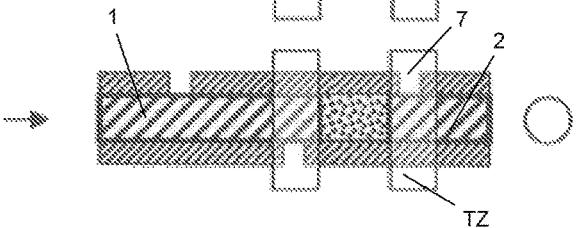
Figure 8H:
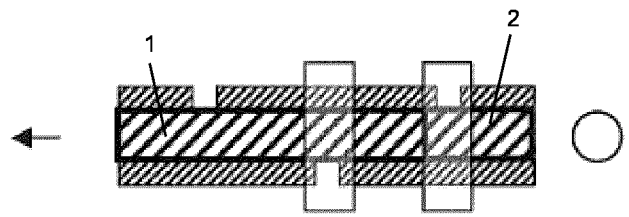
Figure 8I:
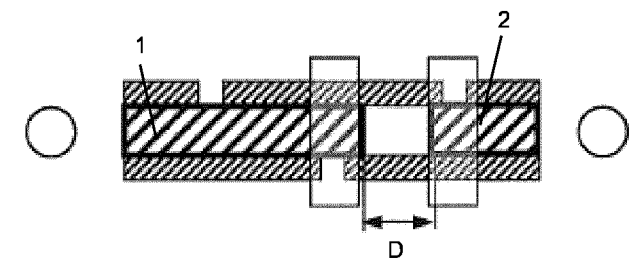
Figure 8J:
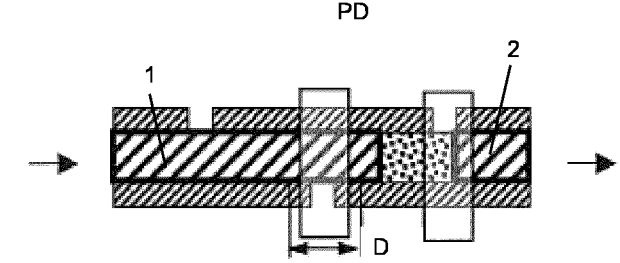
Figure 8K:
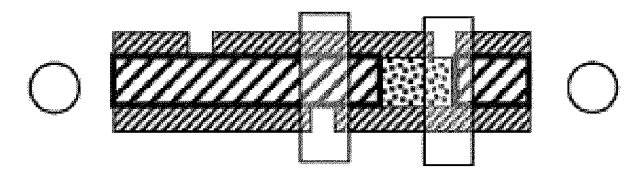

The outer boundary Bo of the further outlet 7 is preferably arranged facing axially away from the inlet 5 (cf. FIG. 8a). As e.g. described in FIGS. 3a to 3d or 4a to 4d, at first, a respective fluid 12 has to be introduced into the chamber space 16 (cf. FIGS. 8a to 8d).

Now, it is again verified or checked, whether the fluid 12 introduced into the chamber space 16 fulfils the compression property requirement and is, thus, not completely compressible. Therefore, the first and the second plunger element 1, 2 and with it the fluid 12 are moved to a position, at which the fluid 12 is fluidly disconnected from an exterior of the chamber 4 (cf. FIG. 8e). Subsequently both plunger elements 1, 2 are locked (cf. FIG. 8f) and compressed until no further relative movement of the first and the second plunger element 1, 2 is possible (cf. FIG. 8g). If the fluid 12 is completely compressible such that the plunger elements 1, 2 e.g. abut and/or the minimum distance MD is reached (cf. FIG. 8h), the presented method requires again to remove the fluid 12 from the chamber space 16 (cf. FIGS. 4i to 4l for instance). Then, a new fluid 12 is introduced into the chamber 4 as described in FIG. 8b onwards. When, as e.g. indicated in FIG. 8g, the fluid 12 in the chamber space 16 fulfils the respective compression property requirement, the fluid 12 can be used to detect the location of the outer boundary Bo of the further outlet 7. Therefore, the fluid 12 is then after a decompression by (back-)movement of the second plunger element 2 (cf. FIG. 8i) replaced towards the tolerance zone TZ of the further outlet 7 (cf. FIG. 8j). Particularly, the fluid 12 or as the case may be the inner side or end of the first plunger element 1 is moved towards the tolerance zone TZ of the further outlet 7.

Said position is preferably axially spaced from the detection position DP by the respective tolerance distance TD.

Figure 8L:
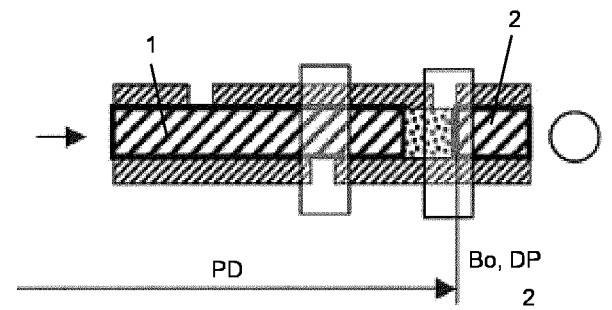
Figure 8M:
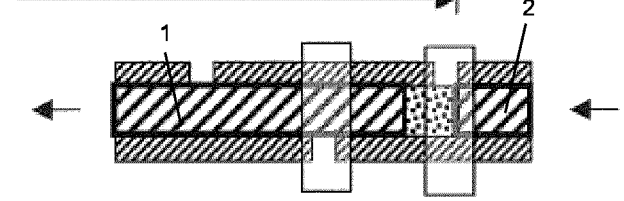

Then, as e.g. shown in FIG. 8l, the second plunger element 2 is locked and the first plunger element 1 compresses or moves the fluid 12 towards the second plunger element 2, i.e. to the right. If, under this compression, the distance D between the first and the second plunger element 1, 2 equals the minimum distance MD, the axial position of the borderline BL between the first and the second plunger element 1, 2 is found and recorded as the location of the outer boundary Bo of the further outlet 7 by the recording unit. If, on the other hand, under said compression, the distance D between the first and the second plunger element 1, 2 does not equal the minimum distance MD, the fluid 12 is moved (to the left in FIG. 8m) to a position being arranged closer to the detection position DP, by the respective predetermined distance PD. A movement as shown in FIG. 8m may (also) be suitable if there is a step between the boundary of the further outlet 7 and the first plunger element 2, for example in a situation similar to FIG. 8l, if the second plunger element is arranged more to the right. This would lead to fluid being trapped between the two plunger elements 1, 2. Then the plunger elements 1, 2 are displaced to the left and the trapped fluid can also be dispensed via the opening (further outlet 7). The procedure described above is repeated until the minimum distance MD is finally reached or preferably the resulting gap between both plunger elements 1, 2 is zero.

The scope of protection is not limited to the examples given herein above. The disclosure is embodied in each novel characteristic and each combination of characteristics, which particularly includes every combination of any features which are stated in the claims, even if this feature or this combination of features is not explicitly stated in the claims or in the examples.

REFERENCE NUMERALS

1 First plunger element
2 Second plunger element
3 Housing
4 Chamber
5 Inlet (opening)
6 Outlet (opening)
7 Further outlet (opening)
10 Control Unit
12 Fluid
16 Chamber space
100 Medical pump
X Longitudinal axis
MD Minimal Distance
RP Reference position
TZ Tolerance Zone
TD Tolerance distance
DP Detection position
D Distance
PD Predetermined distance
BL Borderline
$B_i$ Inner boundary
$B_o$ Outer boundary
B1 First boundary
B2 Second boundary

The invention claimed is:
1. A method of calibrating a medical pump, comprising the steps of:
providing a medical pump comprising a chamber, a first plunger element and a second plunger element, the first and second plunger elements being movable relative to each other and relative to the chamber,
determining a minimum distance between the first plunger element and the second plunger element,
detecting the location of an opening of the chamber, wherein the following steps are carried out to detect the location of the opening:
a) introducing a fluid into a chamber space defined by the first and the second plunger elements, b) ejecting the fluid via the opening until the first and second plunger elements are arranged at the minimum distance relative to each other, and c) determining the location of the opening based on the position of at least one of the first and second plunger elements when the first and second plunger elements are arranged at the minimum distance after step b).

2. The method according to claim 1, wherein
determining the location of the opening of the chamber comprises determining the location of at least one boundary of the opening, and wherein determining the location of the at least one boundary of the opening comprises:
moving the fluid to a position axially spaced from a detection position of the opening by a tolerance distance, and
1) if, under compression of the fluid, the distance between the first and the second plunger element equals the minimum distance, recording the axial position of a borderline between the first and the second plunger elements as the location of the at least one boundary of the opening, and
2) if, under compression of the fluid, the distance between the first and the second plunger elements does not equal the minimum distance, moving the fluid to a position being arranged closer to the detection position, by a predetermined distance, and continuing with step 1).

3. The method according to claim 1, wherein, in step a) and/or before step b) it is detected whether the fluid fulfils a compression property requirement by compressing the fluid while being fluidly disconnected from an exterior of the chamber, wherein, when the fluid does not fulfil the compression property requirement, the fluid is removed from the chamber space and replaced with a new fluid in the chamber space until the fluid in the chamber space does fulfil the compression property requirement.

4. The method according to claim 1, wherein the determination of the minimum distance between the first plunger element and the second plunger element is carried out by an approximative iteration comprising:
moving the second plunger element to an arbitrary position in a tolerance zone of the opening;
moving the first and the second plunger elements relatively towards each other until no further relative movement is possible, and
recording the minimum distance of the first and the second plunger element from the iteration.

5. The method according to claim 1, wherein, before the determination of the minimum distance, the first and the second plunger elements are moved axially away from each other until each of the first and the second plunger elements abuts a stop.

6. The method according to claim 1, wherein the axial positions of the first and/or the second plunger element at which the minimum distance is determined are recorded as a removal positions of the first and the second plunger elements.

7. The method according to claim 2, wherein the tolerance distance is defined by a tolerance zone of the opening.

8. The method according to claim 7, wherein the medical pump comprises a driving unit configured to drive the first plunger element and the second plunger element, and wherein the tolerance zone of the opening is defined by the nominal position of the opening and driving tolerances of the driving unit.

9. The method according to claim 2, wherein the predetermined distance is less than half of a diameter of the opening the location of which should be determined.

10. The method according to claim 2, wherein the medical pump comprises an inlet for receiving a fluid and an outlet for removing the fluid from the chamber, the outlet being axially spaced from the inlet.

11. The method according to claim 10, wherein the opening comprises the inlet and the boundary comprises a first boundary of the inlet.

12. The method according to claim 11, wherein the opening comprises the inlet and the boundary comprises a second boundary of the inlet being arranged axially opposite to the first boundary.

13. The method according to claim 10, wherein the opening comprises the outlet and the boundary comprises an inner boundary of the outlet being arranged facing towards the inlet.

14. The method according to claim 10, wherein the tolerance distance equals half of an axial extension of the opening.

15. The method according to claim 10, wherein the opening comprises the outlet and the boundary comprises an outer boundary of the outlet arranged facing away from the inlet, and wherein the tolerance distance equals the axial extension of the outlet.

16. The method according to claim 10, wherein the chamber comprises a further opening defining one of a second outlet and a second inlet, and wherein the boundary comprises one or more of an inner boundary and an outer boundary of the further opening.

17. A medical pump configured to perform the method of claim 1.

18. The method according to claim 1, wherein the medical pump comprises an inlet for receiving a fluid and an outlet for removing the fluid from the chamber, the outlet being axially spaced from the inlet.

19. The method according to claim 1, wherein the first plunger element and the second plunger element abut at the minimum distance.

20. A method of priming a medical pump comprising the method of claim 1.

* * * * *